United States Patent [19]

Piotrowski et al.

[11] Patent Number: 5,034,549
[45] Date of Patent: * Jul. 23, 1991

[54] OLEFIN POLYMERIZATION CATALYST

[75] Inventors: Andezej M. Piotrowski, Peekskill; Elliot I. Band, North Tarrytown; Johst H. Burk, Mohegan Lake, all of N.Y.

[73] Assignee: Akzo N.V., Arnhem, Netherlands

[*] Notice: The portion of the term of this patent subsequent to Jul. 31, 2007 has been disclaimed.

[21] Appl. No.: 422,324

[22] Filed: Oct. 16, 1989

Related U.S. Application Data

[63] Continuation-in-part of Ser. No. 386,938, Jul. 28, 1989, Pat. No. 4,945,076.

[51] Int. Cl.$^5$ ................................................ C07F 7/02
[52] U.S. Cl. ...................................... 556/10; 502/117
[58] Field of Search ................... 502/117; 556/10, 11

[56] References Cited

U.S. PATENT DOCUMENTS

| | | | |
|---|---|---|---|
| 3,740,384 | 6/1973 | Ballard | 502/156 X |
| 4,752,597 | 6/1988 | Turner | 502/117 X |
| 4,808,561 | 2/1989 | Welborn | 502/117 X |

OTHER PUBLICATIONS

Ballard et al., Die Makromolekulare Chemie 170, 1-9 (1973).
Abstract of Paper No. 562, 23nd International Congress of Pure and Applied Chemistry, Boston, 1971, p. 236.

*Primary Examiner*—Patrick P. Garvin
*Attorney, Agent, or Firm*—Richard P. Fennelly; Louis A. Morris

[57] ABSTRACT

Silicon or siloxane diols react with dicyclopentadienyl zirconium compounds to form catalytically active compositions. These compositions can be used to polymerize ethylene when combined with methylaluminoxane.

8 Claims, 1 Drawing Sheet

OLEFIN POLYMERIZATION CATALYST

RELATED APPLICATION

This is a continuation-in-part of U.S. Ser. No. 386,938, filed Jul. 28, 1989, and now U.S. Pat. No. 4,945,076.

BACKGROUND OF THE INVENTION

U.S. Pat. No. 3,740,384 describes an olefin polymerization catalyst comprising the reaction product of a siloxane-diol and an organometallic zirconium catalyst which may be an alkyl, alkenyl or aralkyl zirconium. Representative organometallic zirconium complexes include those containing allyl, methallyl, methylbenzyl or methylene naphthyl ligands.

D. G. H. Ballard et al., Die Makromolekulare Chemie 170, 1-9 (1973) describe the use of catalysts formed from zirconium compounds and silanols. The zirconium compounds used included tetrabenzylzirconium and tetraallylzirconium.

Ballard indicated (in Abstract of Paper No. 562, 23rd International Congress of Pure and Applied Chemistry, Boston, 1971, p. 236) that replacement of allyl and benzyl ligands on the aforementioned zirconium complexes with halogen atoms gives large increases in polymerization activity whereas introduction of other ligands (including cyclopentadienyl) rendered those compounds inactive for polymerization.

SUMMARY OF THE INVENTION

The instant invention in one embodiment relates to novel cyclopentadienyl zirconium/hydroxy silicon or siloxane compositions. The invention also relates to the use of such compositions in the polymerization of olefins.

DESCRIPTION OF THE DRAWINGS

The Drawings enclosed herewith form a portion of the instant Specification wherein in FIG. 1.

DETAILED DESCRIPTION OF THE INVENTION

It is known to use dicyclopentadienyl zirconium dichloride and methylaluminoxane (MAO) to polymerize ethylene. A high MAO concentration is needed to achieve good polyethylene productivity. If the concentration of MAO is decreased, the productivity of polyethylene drops. Increasing the concentration of zirconium organometallic can increase the productivity but the resulting polymer is of relatively low molecular weight.

The instant invention relies upon the finding that silicon or siloxane diols, if reacted with dicyclopentadienyl zirconium compounds, can yield compositions which are highly active catalysts for ethylene polymerization. These catalysts yield relatively high molecular weight polyethylene, for example, at relatively high concentrations of organometallic zirconium component and relatively low MAO concentration.

The dicyclopentadienyl zirconium component used in forming the novel catalytic compositions may be represented by the formula $Cp_2ZrR_2$, where Cp is cyclopentadienyl and R is alkyl (e.g., methyl) or halogen (e.g., chlorine).

The siloxane or silicon diol used can be represented by the formulae:

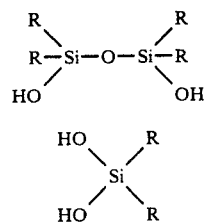

where the R groups may be the same or different and can be alkyl (e.g., $C_1$-$C_4$ alkyl) or aryl (e.g., phenyl).

The relative amounts of organometallic zirconium compound and silicon or siloxane diol which can be reacted range from about 0.1:1 to about 10:1 on a molar basis, most preferably about 0.5:1 to about 2:1.

The catalyst components used herein can comprise from about $10^{-9}$ mole to about $10^{-5}$ mole of the novel zirconium/diol reaction product and about 20 mg to about 1000 mg of methylaluminoxane.

The Examples which follow illustrate certain embodiments of the present invention.

EXAMPLE 1

Figure 1A:
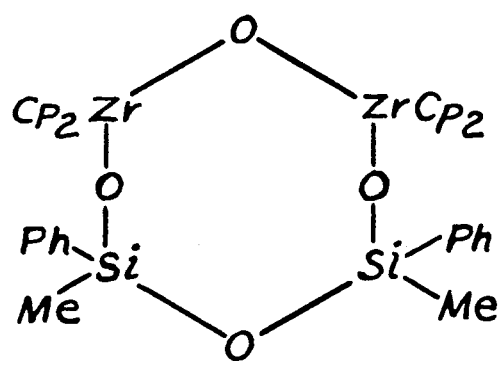
In FIG. 1a [I] represents the structure of the compound made in Example 1, namely, cyclo-1,3 bis(dicyclopentadienylzirconoxy(IV))-5,7; bis-(methylphenylsiloxane)
Figure 1C:
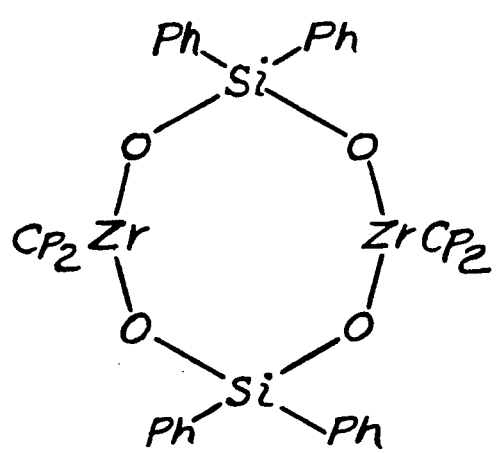
In FIG. 1c [III] represents the structure of the compound made in Example 2, namely, cyclo-1,5-bis(dicyclopentadienylzirconoxy(IV))-3,7 bis(diphenylsiloxane); and In FIG. 1d [IV] represents the structure of the compound made in Example 3, namely, cyclo-1,7 bis(dicyclopentadienylzirconoxy(IV))-3,5,9,11 tetrakis(diphenylsiloxane).
Figure 1B:
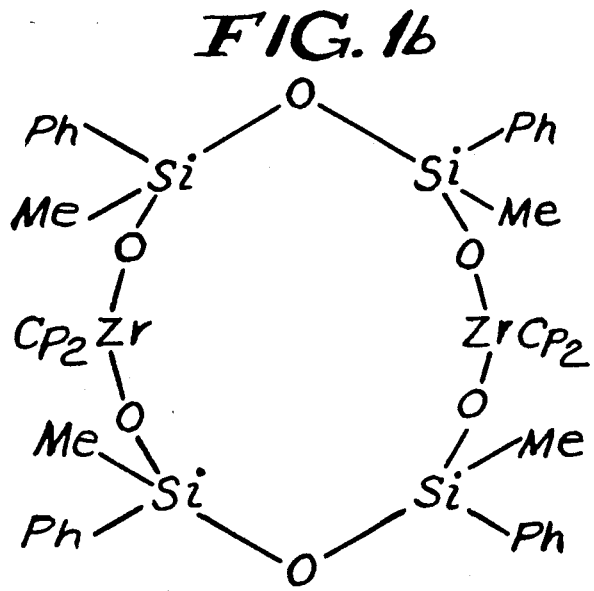
In FIG 1b [II] represents the structure of the second compound made in Example 1, namely, cyclo-1,7 bis(-dicyclopentadienylzirconoxy(IV))-3,5,9,11 tetrakis(methylphenylsiloxane)
Figure 1D:
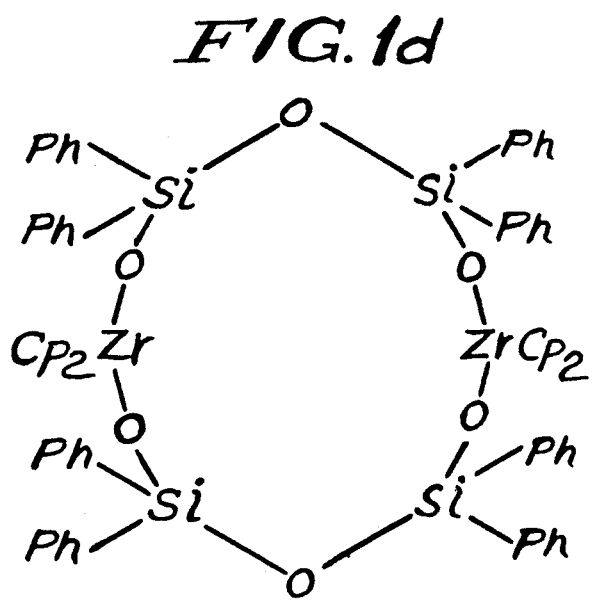

This Example illustrates the preparation of the novel zirconium catalysts (I) and (II) shown in FIG. 1.

Dimethyldicyclopentadienylzirconium(IV), $Cp_2ZrMe_2$, 1.68 gram, was dissolved in 50 ml of diethyl ether, and 6.7 millimoles of HO(Ph)(Me)SiOSi(Me)(Ph)OH dissolved in 15 ml of ether were slowly added. After gas evolution ceased the solvent was evaporated. A white amorphous product was extracted with methylene chloride, and the extract was crystallized from a chloroform/toluene/heptane mixture. 0.102 gram of crystalline material (I) in FIG. 1 was isolated. Some solvent was then evaporated, and the solution was stored overnight in a refrigerator. Another crop of white crystals was formed (0.08 gram) (II) in FIG. 1. The structure of compound I was assigned based on its $^1$HNMR spectrum. The structure of II was determined by single crystal x-ray diffraction.

EXAMPLE 2

This Example illustrates the preparation of the novel zirconium catalyst (III) shown in FIG. 1.

Dicyclopentadienylzirconium dichloride, $Cp_2ZrCl_2$, (2.92 grams) was suspended in 50 ml of diethyl ether and 20 millimoles of methyl lithium in ether were added over a period of ½ hour. The reaction mixture was then stirred at room temperature for one hour, and the solvent was evaporated under vacuum. The product was dissolved in ether and LiCl by-product was separated by filtration to yield a clear solution of dicyclopentadienyldimethylzirconium(IV), $Cp_2ZrMe_2$. Ten millimoles of $HO(Ph)_2SiOSi(Ph)_2OH$ was then dissolved in 50 ml of ether and was combined with the $Cp_2ZrMe_2$ solution. The reaction mixture was then stirred at room temperature for two hours upon which the solvent was evaporated. The white amorphous product was extracted with hot toluene/methylene chloride. The clear solution was then heated for a few minutes and excess methylene chloride was removed in a stream of nitrogen. The solution was left at room temperature for 24 hours and 0.13 gram of white crystals (III) was isolated by filtration. The proton NMR spectrum of the compound (III) showed a Cp/Ph ratio of 1 to 2. The x-ray diffraction analysis of compound (III) and was performed, and the structure of the compound is shown in FIG. 1 as compound III.

Compound III was also prepared in high yield by the reaction of $Cp_2ZrMe_2$ with diphenylsilanediol.

EXAMPLE 3

This reports synthesis of the zirconium catalyst IV shown in FIG. 1.

To a stirred solution of $Cp_2ZrCl_2$ (5.54 millimoles) in ether was slowly added $Ph_2Si(OH)_2$ (1.10 gram). When gas evolution ceased a fluffy white solid was separated by filtration and to the clear reaction mixture more $Ph_2Si(OH)_2$ (0.34 gram) was added. The reaction mixture was allowed to stand overnight and a white crystalline product (1.72 gram) was formed (IV). The x-ray diffraction analysis of compound (IV) was performed. The structure is shown in FIG. 1.

EXAMPLES 4-14

Ethylene polymerizations were conducted in 300 ml toluene in a 500 ml pressure bottle equipped with a mechanical stirrer, thermocouple and pressure transducer. Toluene was purified by passage through molecular sieves and activated alumina columns. Ethylene was purified by passage through activated copper and molecular sieves. The polymerization was initiated by adding methylaluminoxane, then the zirconium catalyst, and pressurizing with ethylene to 47 psig ±1. Ethylene was fed on demand through a gas flow meter. The temperature was maintained at the level given in Table 1 (temperatures above 85.5° C. indicate difficulties in cooling), and the stirring speed was increased as the solution viscosity increased. The polymerization was terminated by venting and quenching with methanol. The polymer was washed with methanol and acetone and was air dried. The results are listed in Table 1 and Table 2. Examples 11 and 12 are presented for comparative purposes.

TABLE 1

| Example No. | Zirconium compound | Zr moles × $10^6$ | $Me_3Al$ mg | MAO (mg) |
|---|---|---|---|---|
| 4 | III | 9 × $10^{-3}$ | — | 330 |
| 5 | IV | 3.6 × $10^{-2}$ | — | 337 |
| 6 | III | 5.5 × $10^{-1}$ | — | 100 |
| 7 | III | 2.4 | — | 80 |
| 8 | II | 3.7 | — | 51 |
| 9 | III | 4.0 | — | 30 |
| 10 | III | 4.0 | 40 | 10 |
| 11 | $Cp_2ZrCl_2$ | 6.55 | — | 31 |
| 12 | $Cp_2ZrCl_2$ | 6.55 | 48 | 30 |
| 13 | III | 6.55 | — | 31 |
| 14 | I | 7.1 | — | 33 |

| Example | Time | Yield | Temp. | |

TABLE 1-continued

| No. | (min) | (grams PE) | (°C.) | Melt Flow* |
|---|---|---|---|---|
| 4 | 9 | 5.73 | 85 | 0.3 (0.8) |
| 5 | 10.75 | 7.73 | 85.3 | — (—) |
| 6 | 8 | 7.76 | 85 | 0.3 (0.9) |
| 7 | 5 | 9.91 | 87 | 1.6 (4.6) |
| 8 | 10 | 20.86 | 86.1 | 10 (—) |
| 9 | 9 | 9.01 | 86 | 2.0 (5.4) |
| 10 | 20 | 18.8 | 85.5 | 10 (—) |
| 11 | 10 | 17.3 | 88.9 | 10 (—) |
| 12 | 9 | 21 | 87 | 19 |
| 13 | 9 | 12.2 | 87 | 2.5 (6.4) |
| 14 | 8 | 15.3 | 87.3 | 12 (—) |

*190° C., 0.0827" orifice, 2160 grams load. (5000 grams load)

TABLE 2

Molecular weights and polydispersity determined by GPC (140° C. in TCB)

| Example No. | $M_w$ | $M_z$ | $M_n$ | $M_{z+1}$ | $M_v$ | PDI |
|---|---|---|---|---|---|---|
| 5 | 116400 | 174000 | 69700 | 240000 | 116400 | 1.67 |
| 6 | 344000 | 550000 | 195000 | 770000 | 344000 | 1.77 |
| 11 | 103800 | 208800 | 69800 | 292800 | 130800 | 1.87 |
| 13 | 216000 | 331000 | 127800 | 462000 | 216000 | 1.69 |

$M_w$ = weight average molecular weight.
$M_z$ = Z-average molecular weight.
$M_n$ = number average molecular weight.
$M_{z+1}$ = Z+1 average molecular weight.
$M_v$ = viscosity average molecular weight.
PDI = polydispersity index = $M_w/M_n$.

The foregoing Examples illustrate certain specific embodiments of the instant invention and should, for that reason, not be construed in a limiting sense. The scope of protection which is sought is set forth in the claims which follow:

We claim:

1. The reaction product of a silicon or siloxane diol and a dicyclopentadienyl zirconium.

2. A product as claimed in claim 1 which is admixed with methylaluminoxane.

3. The product of claim 1 wherein the silicon diol is of the formula

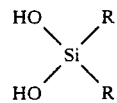

where R is selected from the group consisting of alkyl and aryl.

4. The product of claim 1 wherein the siloxane diol is of the formula

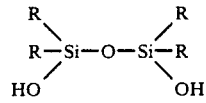

where R is selected from the group consisting of alkyl and aryl.

5. The product of claim 1 which is cyclo-1,3 bis(dicyclopentadienylzirconoxy(IV))-5,7bis(methylphenylsiloxane).

6. The product of claim 1 which is cyclo-1,7 bis(dicyclopentadienylzirconoxy(IV))-3,5,9,11 tetrakis(methylphenylsiloxane).

7. The product of claim 1 which is cyclo-1,5-bis(dicyclopentadienylzirconoxy(IV))-3,7 bis(diphenylsiloxane).

8. The product of claim 1 which is cyclo-1,7 bis(dicyclopentadienylzirconoxy(IV))-3,5,9,11 tetrakis(diphenylsiloxane).

* * * * *

UNITED STATES PATENT AND TRADEMARK OFFICE
CERTIFICATE OF CORRECTION

PATENT NO. : 5,034,549
DATED : July 23, 1991
INVENTOR(S) : A. M. Piotrowski - E. I. Band - J. H. Burk It is certified that error appears in the above—identified patent and that said Letters Patent is hereby corrected as shown below:

Col. 2, line 63, change "(III)" to -- (IV) --;

Col. 3, line 4, delete "(IV)";

Col. 3, lines 14 and 17, change "(III)" to -- (IV) --;

Col. 3, line 19, change "III" to -- IV --;

Example 2, last two lines, delete the sentence therein and insert it immediately after the text now appearing for Example 3;

Col. 3, line 1 of Example 3, change "IV" to -- III --; and

Col. 3, lines 9 and 10 of Example 3, change "(IV)" to -- (III) --.

Signed and Sealed this

Seventeenth Day of August, 1993

Attest:

BRUCE LEHMAN

Attesting Officer

Commissioner of Patents and Trademarks